(12) United States Patent
Weiner et al.

(10) Patent No.: US 9,808,258 B2
(45) Date of Patent: Nov. 7, 2017

(54) DEVICES AND METHODS FOR LUMEN OCCLUSION

(71) Applicant: Boston Scientific Scimed, Inc., Maple Grove, MN (US)

(72) Inventors: Jason Weiner, Grafton, MA (US); Paul Smith, Smithfield, RI (US); Robert B. Devries, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 559 days.

(21) Appl. No.: 14/461,650

(22) Filed: Aug. 18, 2014

(65) Prior Publication Data

US 2015/0057681 A1 Feb. 26, 2015

Related U.S. Application Data

(60) Provisional application No. 61/868,390, filed on Aug. 21, 2013.

(51) Int. Cl.
*A61B 17/04* (2006.01)
*A61B 17/128* (2006.01)
(Continued)

(52) U.S. Cl.
CPC ........ *A61B 17/128* (2013.01); *A61B 17/1285* (2013.01); *A61B 17/12104* (2013.01);
(Continued)

(58) Field of Classification Search
CPC .............. A61B 17/128; A61B 17/1285; A61B 2017/22034; A61B 2017/12018; A61B 2017/00809; A61B 2017/00349; A61B 2017/0641; A61B 17/12013; A61B 17/122; A61B 17/221; A61B 2090/037
See application file for complete search history.

(56) References Cited

U.S. PATENT DOCUMENTS 5,366,459 A * 11/1994 Yoon .................. A61B 17/0057
606/151
6,607,542 B1 * 8/2003 Wild .................... A61B 17/122
606/139

(Continued)

FOREIGN PATENT DOCUMENTS

WO WO 2012/037124 A1 3/2012

*Primary Examiner* — Richard Louis
(74) *Attorney, Agent, or Firm* — Bookoff McAndrews, PLLC (57) ABSTRACT

A system may include an introducer sheath including a retention member configured to anchor the introducer sheath in a natural body lumen having a wall. The system may also have an elongate member extending along a longitudinal axis through a working channel of the introducer sheath. Additionally, the system may have a manipulating portion coupled to a distal end of the elongate member. The manipulating portion may include at least one selectively actuatable member configured to transition between an undeployed configuration and a deployed configuration. In the undeployed configuration, the at least one actuatable member may extend substantially parallel to the longitudinal axis and in at least one position in the deployed configuration, the at least one actuatable member may extend radially outwardly from the longitudinal axis. In the deployed configuration, the manipulating portion and elongate member may be configured to be proximally retracted toward the working channel of the introducer sheath so as to move a distal portion of the wall towards a proximal portion of the wall.

18 Claims, 9 Drawing Sheets

(51) Int. Cl.

| | | |
|---|---|---|
| *A61B 17/12* | (2006.01) | |
| *A61B 17/00* | (2006.01) | |
| *A61B 17/22* | (2006.01) | |
| *A61B 17/122* | (2006.01) | |
| *A61B 17/064* | (2006.01) | |
| *A61B 17/221* | (2006.01) | |
| *A61B 90/00* | (2016.01) | |

(52) U.S. Cl.
CPC ....... *A61B 17/122* (2013.01); *A61B 17/12013* (2013.01); *A61B 17/221* (2013.01); *A61B 2017/00349* (2013.01); *A61B 2017/00809* (2013.01); *A61B 2017/0641* (2013.01); *A61B 2017/12018* (2013.01); *A61B 2017/22034* (2013.01); *A61B 2090/037* (2016.02)

(56) References Cited

U.S. PATENT DOCUMENTS

| | | | |
|---|---|---|---|
| 6,896,682 B1 | 5/2005 | McClellan et al. | |
| 8,162,959 B2 | 4/2012 | Cohen et al. | |
| 2003/0036755 A1 | 2/2003 | Ginn | |
| 2004/0078054 A1* | 4/2004 | Biggs | A61B 17/00234 606/232 |
| 2005/0283179 A1* | 12/2005 | Lentz | A61M 25/0054 606/192 |
| 2007/0282355 A1* | 12/2007 | Brown | A61B 17/122 606/151 |
| 2010/0163054 A1* | 7/2010 | Breznel | A61B 17/12022 128/831 |

* cited by examiner

DEVICES AND METHODS FOR LUMEN OCCLUSION

CROSS REFERENCE TO RELATED APPLICATIONS

This application claims the benefit of U.S. Provisional Application No. 61/868,390, filed Aug. 21, 2013, the disclosure of which is incorporated herein by reference in its entirety.

TECHNICAL FIELD

Embodiments of this disclosure relate to methods and devices for treating a lung, and more particularly, to devices and methods for lung volume reduction. The devices and methods disclosed herein, however, may be used to occlude or otherwise close a lumen or other opening in a patient.

BACKGROUND

Chronic obstructive pulmonary disease (COPD) is a serious progressive lung disease which makes it harder to breathe. It currently affects over fifteen million people in the United States alone and is currently a leading cause of death in the country. The overwhelming primary cause of COPD is inhalation of cigarette smoke, responsible for over 90% of COPD cases. The economic and social burden of the disease is both substantial and increasing.

Figure 1:
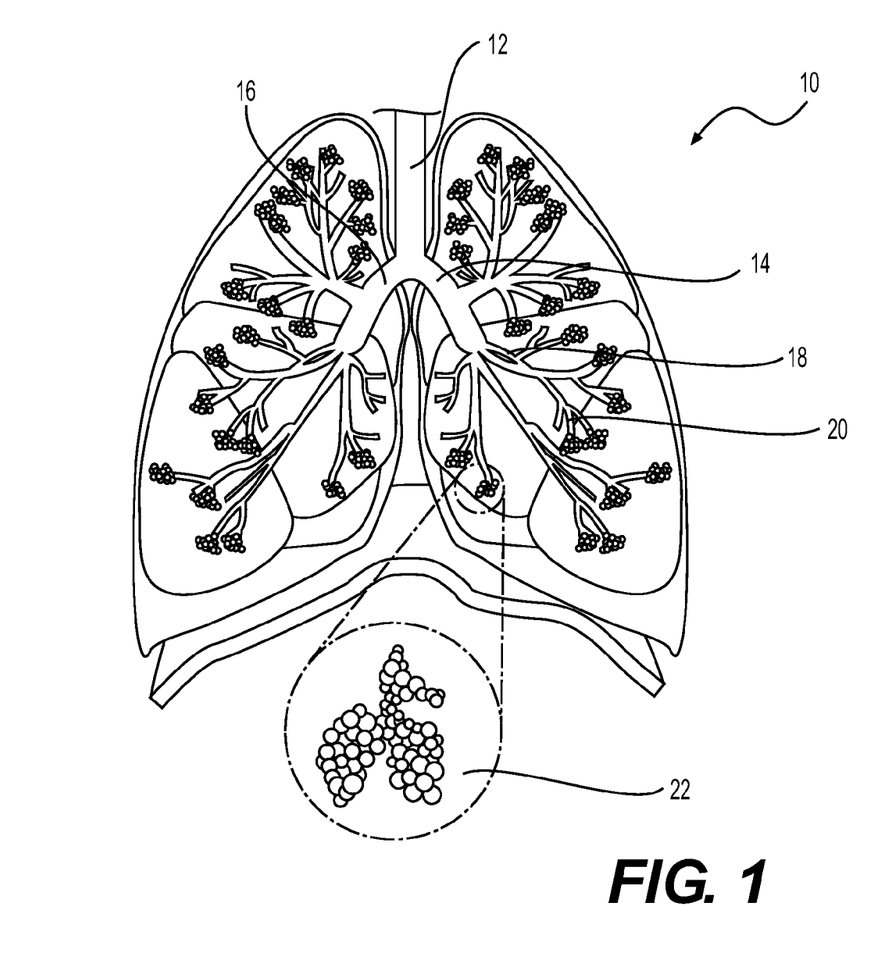
FIG. 1 is a diagrammatic view of healthy lungs.

FIG. 1 depicts a healthy set of lungs 10 in an individual. A wind pipe or trachea 12 connects the nose (not shown) and mouth (not shown) to the lungs 10. As air flows in through the nose and mouth of an individual, the trachea 12 transports the air to the lungs 10 for respiratory functions. The trachea 12 divides into the left 14 and right 16 bronchus stems, which further divide into a plurality of bronchi 18, bronchioles 20, and eventually, terminate in a plurality of alveoli 22. The alveoli 22 are small air sacs which enable gas exchange with the individual's blood stream. That is, they permit oxygen diffusion into the blood stream, and receive and expel $CO_2$ during exhalation.

Figure 2A:
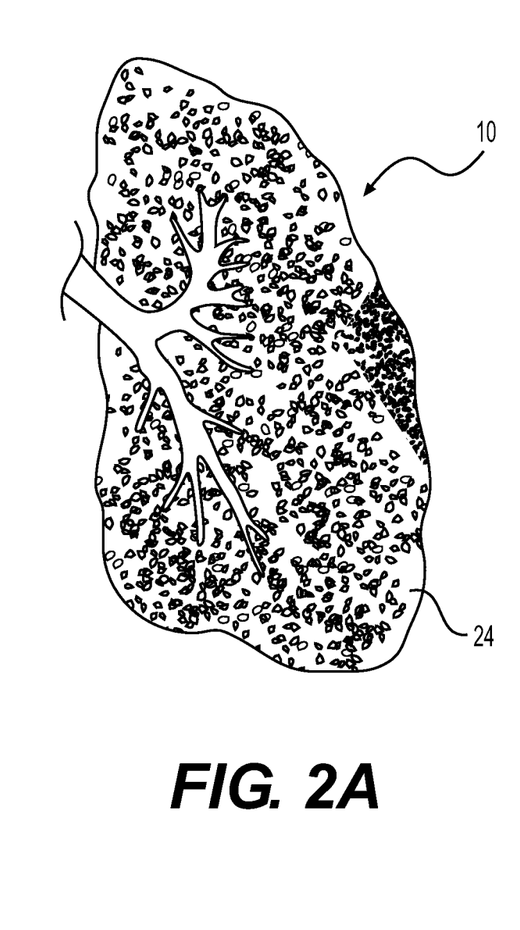
FIGS. 2A and 2B are diagrammatic views of a lung suffering from emphysema.
Figure 2B:
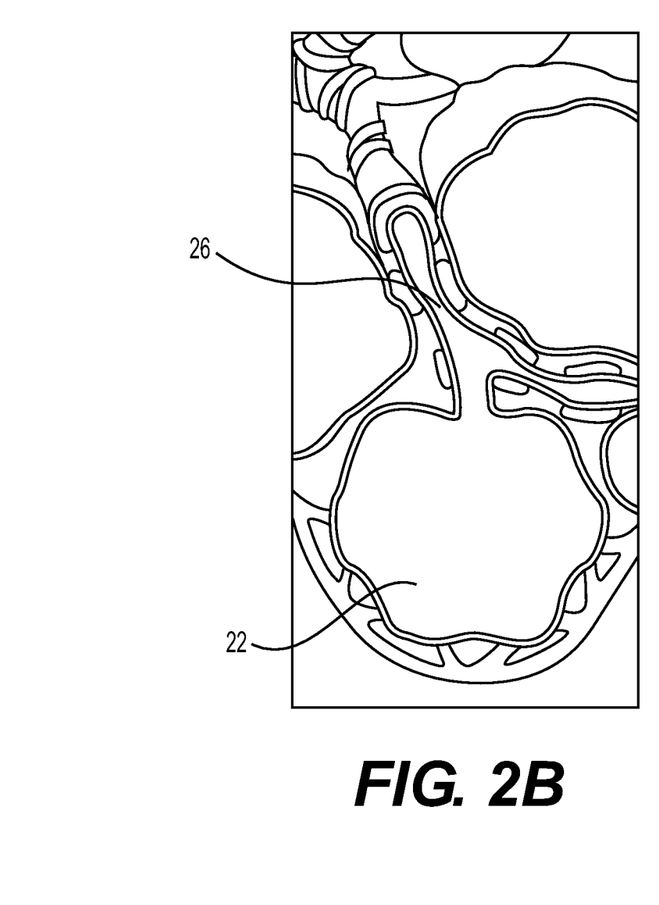

COPD includes emphysema. As shown in FIG. 2A, emphysema may be characterized by the destruction of lung parenchyma 24, the functioning parts of the lungs 10. The parenchyma 24 includes the alveoli 22 walls, bronchioles 20, and the bronchi 18. Destruction of these tissues results in progressively increasing shortness of breath called dyspnea. As it worsens, emphysema turns the healthy alveoli 22, clustered like bunches of grapes, into large, irregular pockets with gaping holes in their inner walls, as shown in FIG. 2B. This reduces the surface area of the lungs and, in turn, the amount of oxygen that reaches an individual's blood stream.

Emphysema also slowly destroys the elastic fibers or tethers that hold open the airways, including the bronchioles 20 and bronchi 18, leading to the alveoli 22. This destruction may cause airways to reduce in diameter or collapse when one breathes out, which prevents the air in your lungs, including $CO_2$, from escaping during exhalation. A significantly reduced diameter airway 26 is depicted in FIG. 2B. A failure to exhale may result in hypercapnia, high blood gas levels of $CO_2$. Hypercapnia can lead to acidosis (lowering of pH levels), which is correlated to a significantly greater risk of mortality in COPD patients.

Treatment may slow progression of emphysema, but it cannot reverse any damage already sustained. Beyond medications and therapy, surgery may be required for treatment of emphysema. Surgery may include lung volume reduction (LVR) surgery, which removes or otherwise decreases damaged tissue in order to assist remaining, healthy tissue to function more efficiently. In severe cases, lung transplant surgery may be necessary.

SUMMARY

Embodiments of the present disclosure relate to, among other things, devices and methods for the treatment of diseased tissue, including tissue suffering from COPD, via lung volume reduction. Each of the embodiments disclosed herein may include one or more of the features described in connection with any of the other disclosed embodiments.

In one embodiment, a system is disclosed. The system may include an introducer sheath including a retention member configured to anchor the introducer sheath in a natural body lumen having a wall. The system may also have an elongate member extending along a longitudinal axis through a working channel of the introducer sheath. Additionally, the system may have a manipulating portion coupled to a distal end of the elongate member. The manipulating portion may include at least one selectively actuatable member configured to transition between an undeployed configuration and a deployed configuration. In the undeployed configuration, the at least one actuatable member may extend substantially parallel to the longitudinal axis and in at least one position in the deployed configuration, the at least one actuatable member may extend radially outwardly from the longitudinal axis. In the deployed configuration, the manipulating portion and elongate member may be configured to be proximally retracted toward the working channel of the introducer sheath so as to move a distal portion of the wall towards a proximal portion of the wall.

The disclosed embodiment may include one or more of the following features: the at least one actuatable member may include a sharpened distal end configured to engage the wall of the lumen; the at least one actuatable member may be configured to transition from the undeployed configuration to the deployed configuration automatically; the at least one actuatable member may be configured to transition from the undeployed configuration to the deployed configuration upon manual activation; the elongate member may include a frangible portion adjacent the manipulating portion; the at least one actuatable member may include a blunt or atraumatic end; the elongate member may include a feature configured to cooperate with a locking member; the at least one actuatable member may be a first member, the system may further include a second selectively actuatable member, the second actuatable member may be configured to transition between an undeployed configuration and a deployed configuration, wherein in the undeployed configuration the second actuatable member may extend substantially parallel to the longitudinal axis, and wherein in at least one position in the deployed configuration, the second actuatable member may extend radially outwardly from the longitudinal axis; each of the first and second actuatable members may be configured to rotate approximately 180° relative to the longitudinal axis so as to occlude the lumen; the elongate member may be configured to be rotated so as to rotate each of the first and second actuatable members about the longitudinal axis; and each of the first and second actuatable members may include scoop-shaped side portions configured to engage and occlude the lumen; and wherein the elongate member may be configured to be axially moved so as to axially move each of the first and second actuatable members along the longitudinal axis, and wherein each of the first and second actuatable members may include a hook-shaped distal end configured to engage and occlude the lumen.

According to another exemplary embodiment, a method of manipulating a lumen is disclosed. The method may include delivering an elongate member into a natural body lumen. The elongate member may extend along a longitudinal axis. A distal end of the elongate member may be coupled to a manipulating head having at least one selectively actuatable member. The method may also include actuating the manipulating head to transition the at least one actuatable member between an undeployed configuration and a deployed configuration. In the undeployed configuration, the at least one actuatable member may extend substantially parallel to the longitudinal axis, and in at least one position in the deployed configuration, the at least one actuatable member may extend radially outwardly of the longitudinal axis. Additionally, the method may include manipulating the lumen via the at least one actuatable member from a position internal of the lumen. Occluding the lumen may include at least one of: moving a distal portion of the lumen toward a proximal portion of the lumen by moving a wall of the lumen at the distal portion away from a central axis of the lumen and back towards the proximal portion, moving the distal portion toward the proximal portion by moving the wall toward the central axis of the lumen and back towards the proximal portion, and twisting the wall of the lumen to collapse the lumen.

The disclosed method may include one or more of the following features: the at least one actuatable member may be automatically actuated; the at least one actuatable member may be manually actuated; the at least one actuatable member may be a first actuatable member, the method further including actuating the manipulating head to transition a second actuatable member between an undeployed configuration and a deployed configuration, such that in the undeployed configuration the second actuatable member may extend substantially parallel to the longitudinal axis, and in at least one position in the deployed configuration, the second actuatable member may extend radially outwardly of the longitudinal axis; actuating the manipulating head may include rotating each of the first and second actuatable members approximately 180° relative to the longitudinal axis so as to occlude the lumen; rotating the elongate member about the longitudinal axis so as to rotate each of the first and second actuatable members about the longitudinal axis, wherein each of the first and second actuatable members may include scoop-shaped side portions configured to engage and occlude the lumen; and axially moving the elongate member along the longitudinal axis so as to axially move each of the first and second actuatable members along the longitudinal axis, wherein each of the first and second actuatable members may include a hook-shaped distal end configured to engage and occlude the lumen.

According another embodiment, a system is disclosed. The system may include an elongate member extending along a longitudinal axis and may be configured for insertion into a natural body lumen. The elongate member may include a feature configured to cooperate with a locking member. The system also may include a manipulating head configured to occlude the body lumen. The manipulating head may include at least three selectively actuatable members configured to transition between an undeployed configuration and a deployed configuration. In the undeployed configuration, the at least three actuatable members may extend substantially parallel to the longitudinal axis, and in at least one position in the deployed configuration, the at least three actuatable members may extend radially outwardly of the longitudinal axis. Additionally, the elongate member may include a frangible portion proximal the manipulating head. Further, the at least three actuatable members and a portion of elongate member distal to the frangible portion may be configured to remain within the lumen to maintain occlusion of the lumen.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Overview

The present disclosure is drawn to devices and methods of treatment of diseased tissue. Such diseased tissue may suffer from COPD. Exemplary embodiments are drawn to devices and methods for lung volume reduction (LVR). LVR is a treatment in which diseased portions of the lungs are killed or otherwise removed from functioning to enable healthy tissue to operate more efficiently. That is, inhaled air is prevented from reaching diseased tissue, allowing the remaining healthy tissue to more readily perform gas exchange. For example, one or more airways of a lung may be closed off or occluded to prevent normal respiratory functions therein. As air is no longer received within the closed off airway, the airway is starved and caused to die. As such, remaining healthy tissues are enabled to receive more air (e.g., the air that once was directed to the now occluded airway). Therefore, a lung 10 may perform respiratory functions more efficiently. While principles of the present disclosure are described herein with reference to treatments for the lungs of a patient, it should be understood that the disclosure is not limited thereto. Rather, the devices and methods may find applicability to occlude any luminal tissue structure.

Exemplary Embodiments

Figure 3:
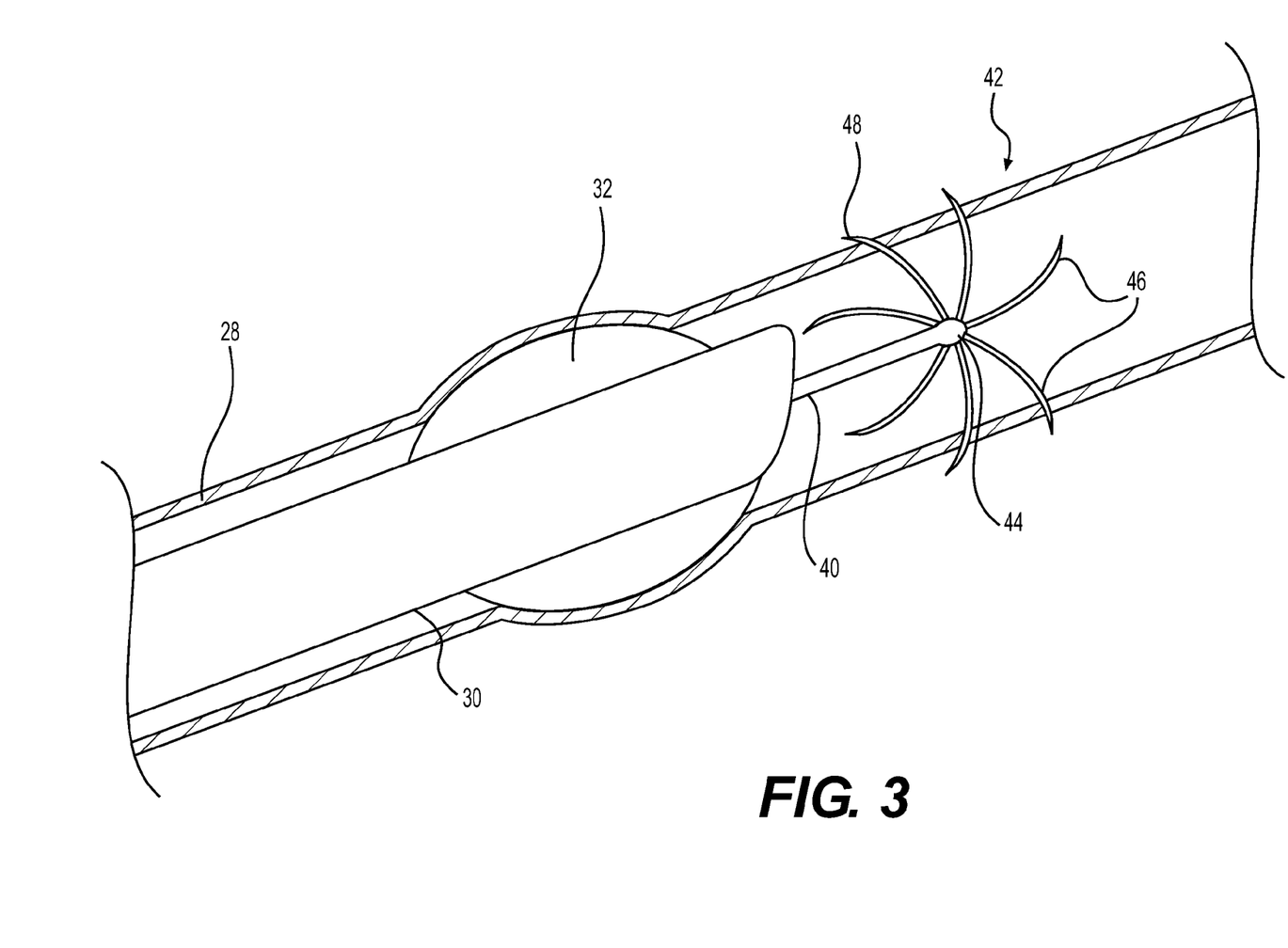
FIG. 3 is a cross-sectional view of an airway including an exemplary embodiment of a device therein.

FIG. 3 depicts a lung airway 28 including an exemplary embodiment of a device therein. Airway 28 may be any of bronchi 18, bronchioles 20, and alveoli 22. Airway 28 may include diseased tissue, or may be positioned adjacent of diseased tissue. A physician may introduce a medical device, such as, for example, an introducer sheath 30 through the patient's airway 28 until a distal end of the sheath 30 reaches a target tissue area within airway 28. Sheath 30 may be introduced into airway 28 via any appropriate method, including being deployed through the airway 28 independently of other medical devices, and being deployed through a lumen of a bronchoscope, catheter, endoscope, or the like. While sheath 30 is referred to and described herein, it is to be understood that any luminal delivery device (e.g., endoscope, bronchoscope, catheter, etc.) may be used without departing from the scope of the disclosure. Sheath 30 may be sized to access the bronchi 18, bronchioles 20, and/or alveoli 22. For example, such bronchoscopes may include at least one working channel (not shown) having an outer diameter of 2 mm or less. The sheath 30 may include a light source, such as, for example, a fiber optic cable or bundle, one or more light-emitting diodes (LED), and/or any other source of light sized for placement within a sheath 30. Additionally, sheath 30 may include a camera or vision system configured to receive images and relay them to a physician via a display device. The vision system may include an image sensor such as, for example, a CMOS or CCD image sensor.

As shown in FIG. 3, the sheath 30 may optionally include a retention member such as, for example, balloon 32, configured to transition between a first uninflated configuration (not shown), and a second expanded configuration. Balloon 32 may expand within airway 28 so as to maintain the position of sheath 30 within airway 28. Accordingly, balloon 32 may be configured to receive a source of inflation fluid through an inflation channel (not shown) in sheath 30. In use, sheath 30 may be in introduced into airway 28 while the balloon is positioned in the first uninflated configuration. Upon reaching the target tissue area within airway 28, the balloon 32 may be inflated so as to transition to the second inflated configuration as shown in FIG. 3. Alternatively, any suitable expandable member may be employed such as, for example, mechanical expansion cages, expandable foam members, hook and/or finger members, and expanding members activated by body heat or chemistry. Additionally or alternatively, balloon 32, or any alternative expanding member, may include agents or drugs such as, for example, antimicrobial agents, analgesics, and anesthetics, etc.

The working channel may be used to pass medical tools into airway 28. An exemplary medical tool is depicted in FIG. 3 and includes an elongate member 40. The elongate member 40 may be configured to pass through the working channel and deliver a manipulating head or device head 42 to the target tissue area with airway 28. That is, elongate member 40 may be configured to extend distally of a distal end face of sheath 30 and position device head 42 proximate the target tissue area. Elongate member 40 may include one or more lumens (not shown) extending therethrough. Additionally, elongate member 40 may include one or more radiopaque markers so as to assist a user in determining the proper location of elongate member 40 within airway 28.

Device head 42 includes a base member 44 configured to support one or more manipulating members or fingers 46. Base member 44 may be coupled to (via e.g., welding, adhesives, mechanical connectors, or monolithically formed from a single continuous piece of material) elongate member 40, and may have any cross-sectional shape appropriate to traverse the working channel and support the one or more fingers 46. For example, as shown in FIG. 3, base member 44 may be ovular. Alternatively, base member 44 may be spherical, square, rectangular, or any other shape sized to pass through the working channel. Preferably, base member 44 may have a rounded distal-most tip so as to be atraumatic during delivery of device head 42 into airway 28. It is to be understood, however, that in some embodiments, base member 44 may be omitted and fingers 46 may be coupled directly to elongate member 40.

The one or more fingers 46 may be configured to expand radially outwardly from base member 44. For example, as shown in FIG. 3, device head 42 includes seven fingers 46. It is understood, however, any number of fingers 46 may be used. Fingers 46 may be configured to transition between a first undeployed configuration (FIG. 7) and a second deployed configuration. In the undeployed configuration, fingers 46 may extend substantially along or parallel to a longitudinal axis of elongate member 40. In other words, fingers 46 may assume a collapsed state in the undeployed configuration such that fingers 46 may pass through the working channel of sheath 30. While fingers 46 are shown extending distally in the first undeployed configuration (FIG. 7), it is to be understood that fingers 46 may extend in a proximal direction substantially parallel with or along the longitudinal axis of elongate member 40 in the undeployed configuration without departing from the scope of the disclosure.

After positioning the medical device at a suitable target site, fingers 46 may be moved to their deployed state, as shown in FIG. 3. As such, fingers 46 may expand radially outwardly from base member 44. Fingers 46 may expand outward either automatically, or upon actuation, as will be explained in more detail later. Fingers 46 may be configured, once deployed, to snag or "catch" tissue within airway 28. Alternatively, fingers 46 may be configured, once deployed, to pierce the wall of airway 28. As such, fingers 46 may include sharpened outer ends 48. In an alternative embodiment, fingers 46 may include suction members on a distal end thereof. That is, each finger 46 may include a channel (not shown) in fluid communication with a vacuum source (not shown). Upon activation of the vacuum source, vacuum pressure may be applied to a wall of airway 28 via the channel so as to suck the wall towards fingers 46, thereby maintaining engagement with the wall of airway 28. In this manner, fingers 46 may grasp a wall of airway 28 without causing trauma.

In use, fingers 46 may be configured to assist in occluding airway 28. For example, in order to perform LVR surgery, or any other lumen occlusion operation, a luminal delivery device such as sheath 30 may be introduced into an airway 28. Upon reaching a target tissue area within airway 28, a retention member, such as, for example, balloon 32, may be optionally deployed. That is, balloon may be inflated so as to transition from a first uninflated configuration, to a second inflated configuration. In the second inflated configuration, balloon 32 may anchor or otherwise retain sheath 30 in place within airway 28. Such anchoring may prevent or inhibit accidental dislodging of sheath 30 during a procedure. Additionally, balloon 32 may be used to, position, center, and/or align sheath 30 in airway 28.

After anchoring sheath 30 within airway 28, a medical device may be deployed through the working channel (not shown) of sheath 30. As such elongate member 40 may be advanced distally past the distal-most end face of sheath 30 so as to position device head 42 within airway 28. Upon advancement of elongate member 40 outward of the working channel of sheath 30, fingers 46 may radially expand outward from base member 44. As will be described in further detail below, fingers 46 may be configured to expand either automatically or upon actuation. As shown in FIG. 3, once deployed, fingers 46 snag or grasp tissue or pierce a wall of airway 28 via sharpened distal ends 48.

Figure 4:
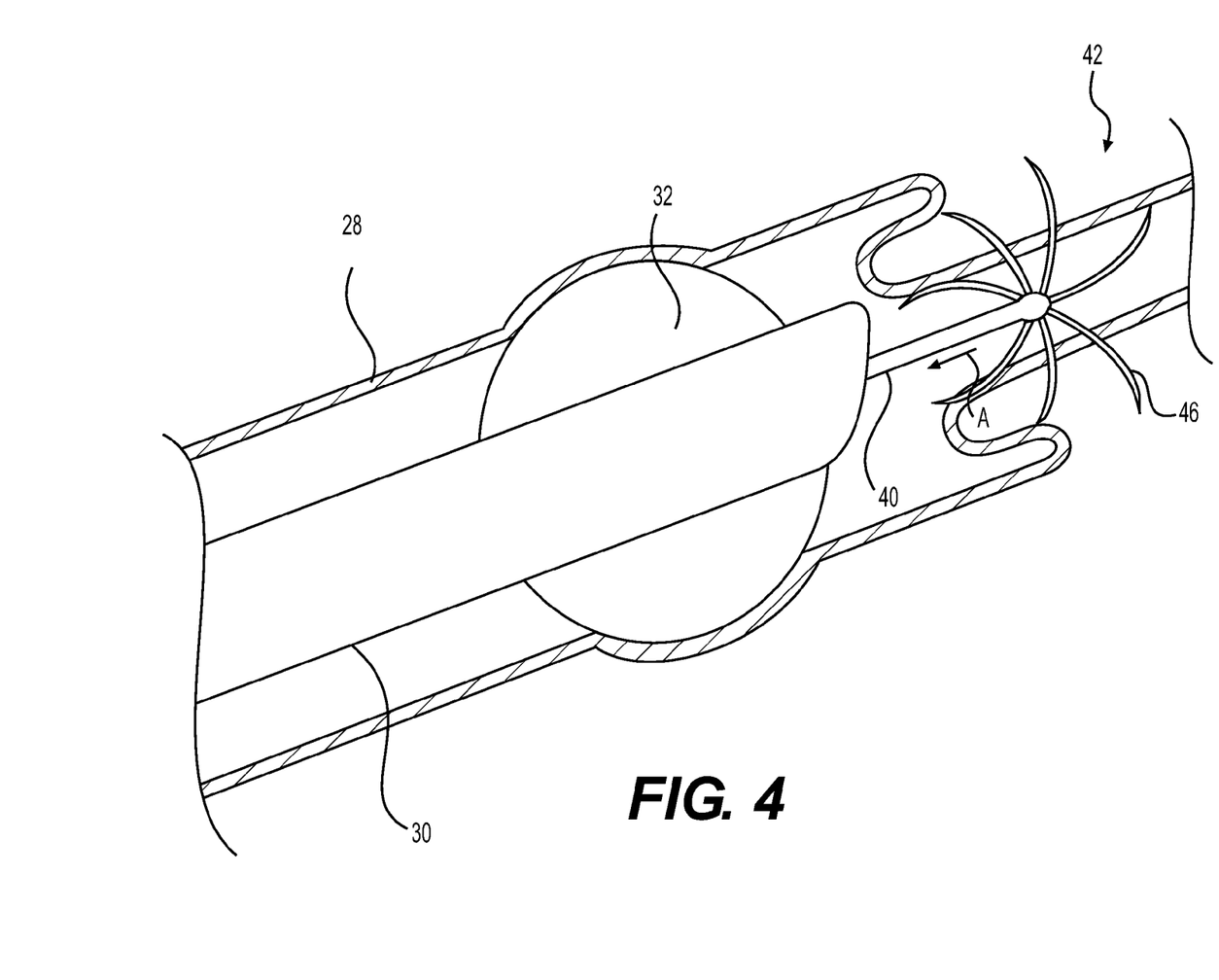
FIG. 4 is a cross-sectional view of an airway including the device shown in FIG. 3 having been moved proximally within the airway.
Figure 5:
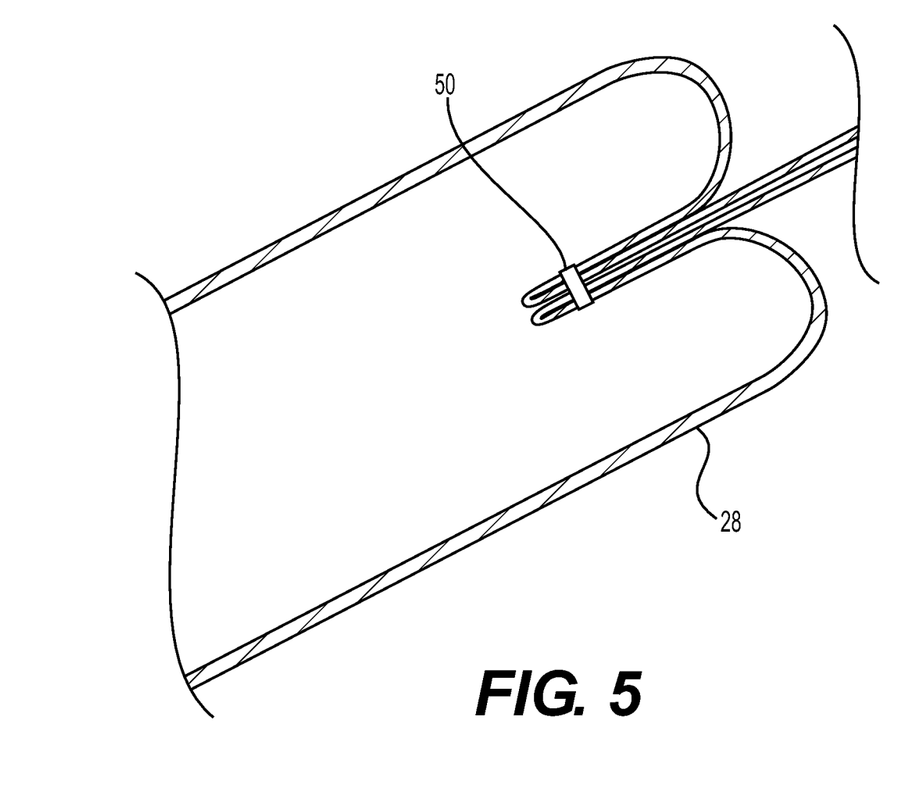
FIG. 5 is a cross-sectional view of an occluded airway.

After fingers 46 are sufficiently embedded in tissue and/or pierced through the wall of airway 28, elongate member 40 may be moved, for example, pulled proximally to involute or otherwise invert the walls of airway 28. That is, as shown in FIG. 4, elongate member 40 and device head 42 may be moved in the direction of arrow A towards and into sheath 30. As elongate member 40 is moved, fingers 46 may pull a distal portion of airway 28 towards a proximal portion of airway 28 so as to fold airway 28 in on itself. As such, the distal portion of airway 28 is moved toward the proximal portion of airway 28 by moving a wall at the distal portion toward a central axis of the lumen and back towards the proximal portion. That is, movement of elongate member 40 in direction A results in involution of airway 28. As shown in FIG. 5, after involution of airway 28, an LVR device 50, such as, for example, a ligation band or clip, may be deployed about the involuted airway 28, so as to occlude or otherwise close airway 28. That is, after folding airway 28 in on itself, LVR device 50 may be deployed so as to close off airway 28 and achieve lung volume reduction. LVR device 50, such as a ligation band or clip, may be biocompatible. Optionally, LVR device 50 may be drug-eluting so as to promote proper tissue healing or sealing following a procedure. Alternatively, after involution of airway 28, a cauterization member (not shown) may be delivered to the closed airway 28. In this embodiment, the cauterization member may be used to deliver energy, e.g., heat, to the closed airway so as to seal (e.g., melt together) tissue at the target site. Optionally, after removal of cauterization member, LVR device 50 may be deployed so as to maintain occlusion of airway 28.

Upon deployment of the LVR device 50, elongate member 40 and device head 42 may be removed. Alternatively, elongate member 40 may be frangible at a distal portion adjacent to and proximal of device head 40. In such an embodiment, after deployment of the LVR device 50, a user may apply a proximally directed force on elongate member 40 so as to break off device head 42 from elongate member 40. As such, device head 42 may be configured to remain within airway 28, as will be described in greater detail below. In such an embodiment, device head 42 may form a portion of LVR device 50 and may be biocompatible. Additionally or alternatively, a proximally extending member may be directed to a frangible portion so as to break off device head 42 from the remainder of elongate member 40.

Figure 6:
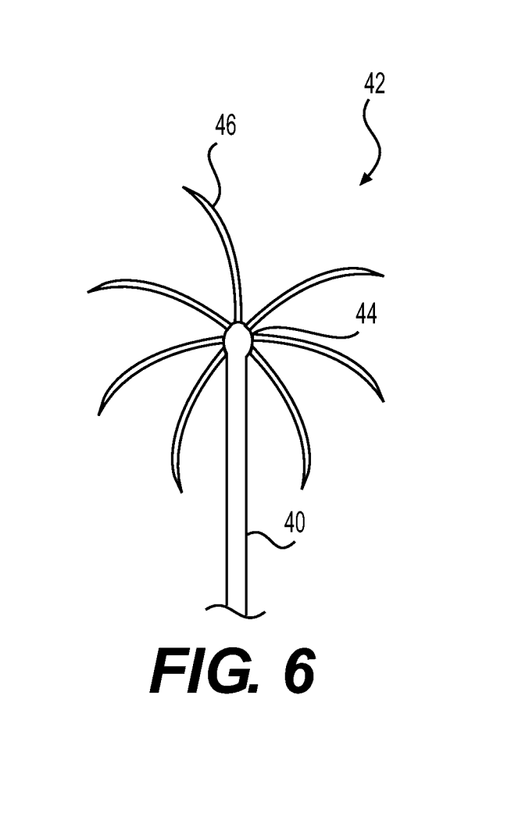
FIG. 6 is an diagrammatic view of an exemplary device.
Figure 7:
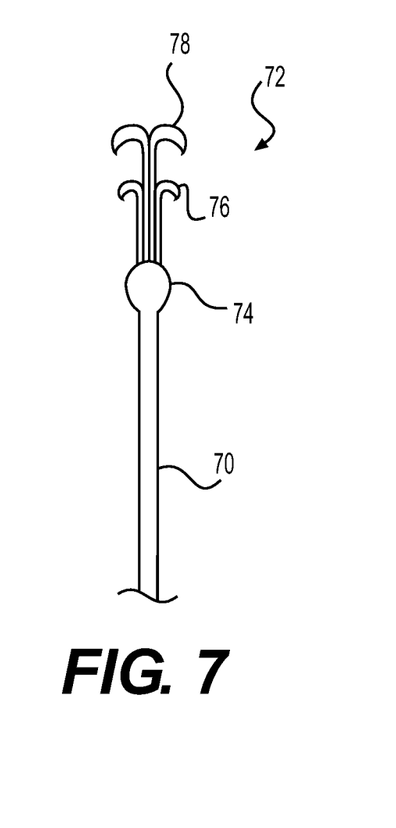
FIG. 7 is a diagrammatic view of an alternative exemplary device.
Figure 8:
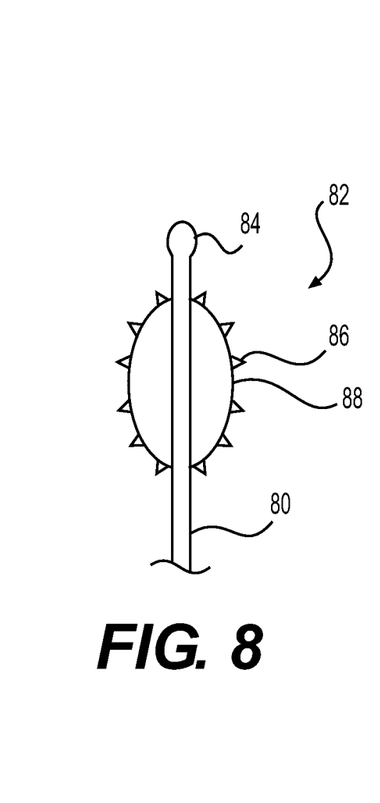
FIG. 8 is a diagrammatic view of an additional, alternative exemplary device.

FIGS. 6-8 depict various exemplary configurations of medical devices in accordance with this disclosure. For example, FIG. 6 depicts, similarly to FIGS. 3 and 4, an elongate member 40 and device head 42. Device head 42 includes a base member 44 and one or more radially expanding fingers 46 extending away from base member 44. Fingers 46 may be configured to deploy automatically upon reaching the target tissue area within airway 28. That is, fingers 46 may be made of a shape memory alloy (SMA) material, such as, for example, NITINOL™. Such a class of materials, upon activation (e.g., application of heat and/or exposure to body chemistry), reform to a "remembered" shape. That is, upon application of an activating force, fingers 46 may spring open to an outwardly deployed "remembered" configuration. Alternatively, fingers 46 may be biased toward the second deployed configuration. In such an arrangement, a sheath (not shown) may be placed over elongate member 40 and device head 42 so as to maintain fingers 46 in the first undeployed configuration. Once positioned within airway 28, the sheath may be removed from device head 42 by moving the sheath and device head 42 relative to one another. Once device head 42 has been uncovered from the sheath, fingers 46 automatically move towards the second deployed configuration.

In yet another embodiment, fingers 46 may be manually actuated so as to move between the first, undeployed configuration and the second, deployed configuration. In such an embodiment, for example, a pull wire may be coupled with a proximal end of fingers 46. For example, in such an embodiment, elongate member 40 may be hollow so as to receive a pull wire therethrough. Additionally, fingers 46 may be pivotally or rotably connected to head 44. Upon application of a proximally directed pulling force on fingers 46 (or on a linkage (not shown) connecting the proximal ends of fingers 46), fingers 46 may move from the first, undeployed configuration (FIG. 7) to the second deployed configuration (FIG. 6).

In another exemplary embodiment, as shown in FIG. 7, fingers 76 may be atraumaticly shaped in the undeployed configuration so as to facilitate advancement into and out of the patient's body. For example, as shown in FIG. 7, fingers 76, extending from base member 74, may have rounded, blunt distal ends 78. In such an embodiment, device head 72 and elongate member 70 may extend distally of the working channel without causing injury or snagging, catching, or piercing tissue of airway 28. Upon placement at a desired location within airway 28, fingers 76 may be moved from the first, undeployed configuration to the second, deployed configuration. Fingers 76 may be moved either manually or automatically.

As shown in FIG. 8, fingers 86 may be selectively deployed via an expandable member, such as, for example, balloon 88. In such an embodiment, fingers 86 may be configured as barbs, sharp points, and/or hooks positioned on an exterior surface of balloon 88. Alternatively, fingers 86 may have any shape configured to snag, catch, or pierce tissue. Additionally, elongate member 80 may be in communication with a source of inflation fluid (not shown) for delivery to balloon 88 via an internal fluid delivery lumen (not shown) in elongate member 80. In such an embodiment, elongate member 80 and device head 82 (including base member 84 and balloon 88) may be introduced into airway 28 via sheath 30 in the first, undeployed configuration in which balloon 88 is deflated so as to lie substantially flat along an exterior surface of elongate member 80. Upon proper positioning within airway 28, balloon 88 may be inflated so as to expand fingers 86 radially outward toward the second, deployed configuration as shown in FIG. 8. It is to be understood that balloon 88 may have any desired expanded shape such as, for example, spherical, ovular, irregular, etc. Alternatively, any suitable expandable member may be employed such as, for example, mechanical expansion cages, expandable foam members, and expanding members activated by body heat or chemistry.

Figure 9:
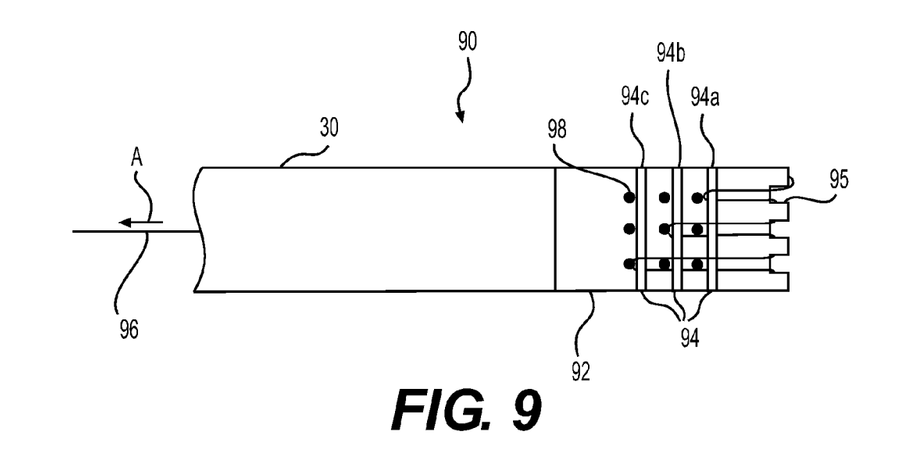
FIG. 9 is a diagrammatic view of an exemplary occlusion delivery device.

Turning now to FIG. 9, an exemplary occlusion delivery device 90 is shown. Occlusion delivery device 90 may be configured to deliver one or more LVR devices, such as, for example, ligation bands 94 to occlude airway 28 (FIG. 5). As such, occlusion delivery device 90 may include a distal cap 92 configured for selective coupling, via friction fit or otherwise, to sheath 30, or another suitable elongate sheath, which may be configured to be advanced to the target site. Distal cap 92 may be made of a transparent material so as to allow the camera or vision system of sheath 30 to receive images of airway 28 without obstruction. One or more ligation bands 94 may be positioned about distal cap 92. That is, ligation bands 94 may be stretched (from a relaxed neutral configuration to an expanded stressed configuration) so as to be snuggly held about the distal cap 92. In the embodiment shown in FIG. 9, three ligation bands 94a-c are arranged about the distal cap 92 from a distal end to a proximal end of distal cap 92. Those of ordinary skill will recognize that a greater or lesser number of ligation bands may be employed in accordance with the principles of the present disclosure. Optionally, distal cap 92 may include one or more protrusions 98 configured to maintain a desired alignment and/or position of the one or more ligation bands 94.

As shown in FIG. 9, an actuation member 96 may be used to deploy one or more ligation bands about the involuted airway 28 (FIG. 5). Actuation member 96 may be a wire, cord, or string wrapped about each ligation band 94 and extending proximally through a lumen of distal cap 92 and sheath 30. While a single, continuous actuation member 96 is shown, it is to be understood that a plurality of actuation members 96, corresponding in number to the one or more ligation bands 94, may be employed. Optionally, distal cap 92 may include one or more guides 95 configured to facilitate positioning actuation member 96 about the one or more ligation bands 94.

In use, an operator may involute airway 28 as described above with respect to FIGS. 3-8. Next, the operator may pull on actuation member 96 in the direction of arrow A so as to urge the one or more ligation bands 94 towards a distal end of distal cap 92. For example, in the embodiment shown in FIG. 9, as actuation member 96 is moved in the direction of arrow A, ligation band 94a is engaged and caused to roll or slide toward a distal end of distal cap 92, and finally, fly off (e.g., be pulled off) the distal cap 92 and positioned about involuted airway 28. Any desired number of ligation bands 94 may be used. Optionally, sheath 30 may be in fluid communication with a source of vacuum pressure (not shown). In such an arrangement, the source of vacuum pressure may be used to assist in maintaining involuted airway 28 in proper position to receive the one or more ligation bands 94. In other words, the source of vacuum pressure may be activated so as to suck involuted airway 28 into the lumen of the distal cap 92.

Figure 10:
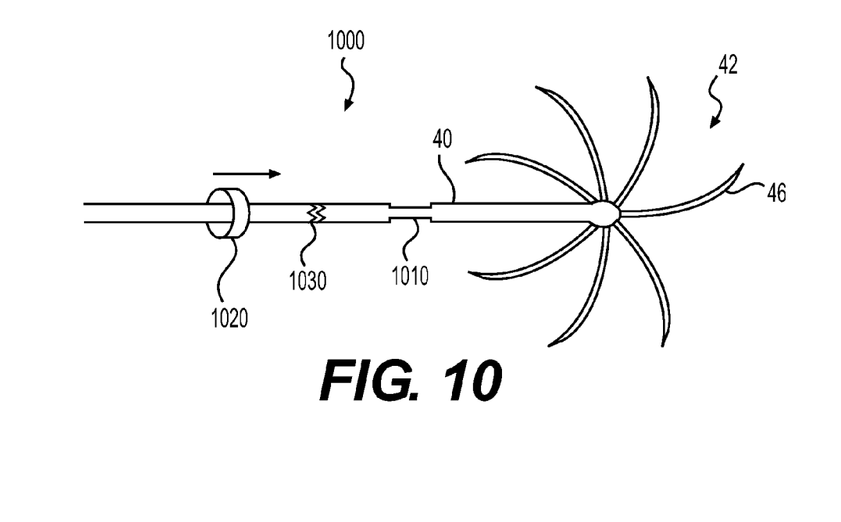
FIG. 10 is a diagrammatic view of an alternative, exemplary occlusion delivery device.

An alternative, exemplary occlusion delivery device 1000 is shown in FIG. 10. Exemplary occlusion delivery device 1000 may include an elongate member 40 and a device head 42 as discussed with respect to FIGS. 3-6. It is to be understood, however, that occlusion delivery device 1000 may additionally or alternatively include one or more features of the exemplary devices described in connection with FIGS. 7 and 8 (e.g., atraumatic fingers 78 and/or balloon 88 or another suitable expandable member). In this exemplary embodiment, elongate member 40 may include a feature configured to cooperate with a locking member 1020. For example, elongate member 40 may include a detent 1010 sized and configured to receive and retain a locking member 1020. In other words, detent 1010 and locking member 1020 may have complimentary engagement surfaces to maintain the relative position of locking member 1020 relative to detent 1010 such as by friction fit, snap-fit, interference fit, or press-fit engagement. For example, locking member 1020 may be stretched about elongate member 40 in a first configuration while detent 1010 may be configured as a reduced dimension (e.g., diameter) portion of elongate member 40. Upon being received within detent 1010, locking member 1020 may be urged into a second substantially unstretched (e.g., neutral) configuration within detent 1010. Once received within detent 1010, locking member 1020 is prevented from sliding along elongate member 40 or otherwise moving out of detent 1010.

In use, elongate member 40 and device head 42 may be used to involute airway 28, as described with respect to FIG. 4 above. After airway 28 has been involuted, an operator may move (e.g., slide) locking member 1020 distally, until locking member 1020 is received within detent 1010. Alternatively, elongate member 40 may be moved proximally relative to locking member 1020. An operator may move locking member 1020 through any appropriate means, such as, for example, urging locking member 1020 distally through the use of a push/pull wire or other medical device passed through sheath 30. Once locking member 1020 is received within detent 1010, involuted airway 28 is compressed between locking member 1020 and device head 42 so as to occlude airway 28. Optionally, a portion of the wall of airway 28 may be compressed between locking member 1020 and detent 1010. In this manner, device head 42 and locking member 1020, in conjunction with detent 1010, cooperate as LVR device 50. In this embodiment, after deployment of the LVR device 50, the operator may apply a proximally directed force on elongate member 40 so as to break off device head 42 from elongate member 40 at frangible portion 1030. Alternatively, frangible portion 1030 may be configured to separate upon application of rotational force. As such, device head 42 may be configured to remain within airway 28 after occlusion. It is to be understood that while sliding locking member 1020 and correspondingly shaped detent 1010 has been described and shown, other arrangements for securing involuted tissue against elongate member 40 are possible. For example, elongate member 40 may be provided with a male threaded portion on an exterior surface thereof, and locking member 1020 may be provided with a female threaded portion on an internal surface thereof. As such, locking member 1020 and elongate member 40 may act in the same manner as a nut and bolt arrangement. Also, it is to be understood that frangible portion 1030 may be replaced by a selectively separable two-piece elongate member 40. That is, elongate member 40 may include male and female threads configured to selectively separate from one another upon rotational force.

Figure 11A:
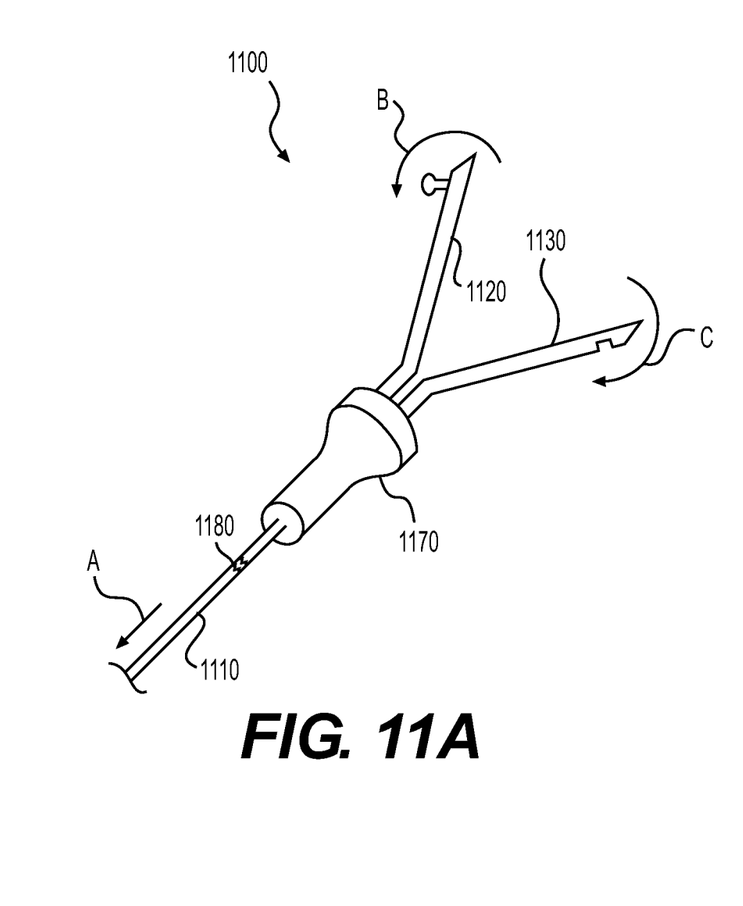
FIGS. 11A and 11B are diagrammatic views of an exemplary device in accordance with a further embodiment of the design.
Figure 11B:
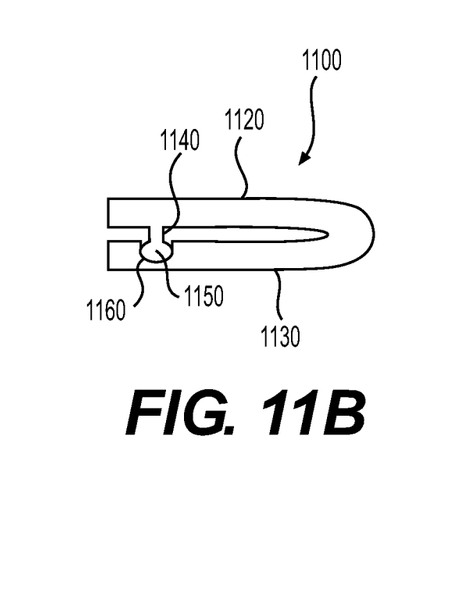

FIGS. 11A, 11B, 12, and 13, depict alternative exemplary occlusion devices according to the present disclosure. For example, as shown in FIGS. 11A and 11B, an exemplary occlusion device may be in the form of a clip 1100 arranged on a distal end of a clip delivery member 1110. In such an embodiment, clip 1100 may act as an LVR device 50. Clip delivery member 1110 may be similar to elongate members 40, 70, and/or 80 described above. As such, clip delivery member 1110 may be configured to pass through a working channel of sheath 30 and deliver clip 1100 to the target tissue area with airway 28. That is, clip delivery device 1110 may be configured to extend distally of a distal end face of sheath 30 and position clip 1100 proximate the target tissue area within airway 28. Additionally, clip delivery device 1110 may include a frangible distal portion 1180 adjacent to clip 1100. In such an embodiment, after deployment of clip 1100 as described below, a user may apply a proximally directed force on clip delivery device 1110 so as to break off clip 1100 from clip delivery device 1110 at frangible distal portion 1180. Therefore, clip 1100 may be configured to remain within airway 28.

Clip 1100 may interact with airway 28 similarly to device heads 42, 72, and 82 described above. That is, clip 1100, including manipulating members such as first and second legs 1120 and 1130, may be employed to snag or catch tissue within airway 28. As such, legs 1120 and 1130 may include textured and/or roughened outward facing surfaces so as to grip tissue during operation. Additionally or alternatively, one or both of legs 1120 and 1130 may include sharpened hooks or tissue piercing members to aid in gripping tissue during operation. Each of legs 1120 and 1130 may be introduced into airway 28 via clip delivery device 1110 in a first substantially straight configuration. That is, each of legs 1120 and 1130 may extend substantially along or parallel to a longitudinal axis of clip delivery device 1110.

Upon reaching a target location within airway 28, clip 1100 may be actuated so as to rotate, pivot, bend, turn, or otherwise move legs 1120 and 1130 in the directions shown by arrows B and C, thereby folding airway 28 in on itself so as to occlude airway 28. That is, legs 1120 and 1130 may be configured to move a distal portion of a wall of airway 28 toward a proximal portion of airway 28 by moving the distal portion away from a central axis of the lumen and back towards the proximal portion. Clip 1100 may be actuated in any appropriate manner, for example, via a push/pull wire extending through clip delivery device 1110 (not shown). Legs 1120 and 1130 may be configured to rotate approximately 180°. For example, legs 1120 and 1130 may transition from the first substantially straight configuration to a second substantially closed configuration as shown in FIG. 11B. In the substantially closed configuration, clip 1100 may be configured to capture and occlude tissue between legs 1120 and 1130. Each of legs 1120 and 1130 may include a geometrical feature to maintain legs 1120 and 1130 in the closed configuration as shown in FIG. 11B. For example, leg 1120 may include a protrusion 1140 having an enlarged distal end 1150, while legs 1130 may include a corresponding cavity or pocket 1160 sized to receive the distal end 1150 of protrusion 1140. Enlarged distal end 1150 and pocket 1160 act as a one-way lock preventing the undesired opening of clip 1100.

Additionally or alternatively, a sheath or housing 1170 may be used to maintain clip 1100 in a closed configuration. For example, housing 1170 may be positioned about clip delivery device 1110 adjacent clip 1100. After moving legs 1120 and 1130 from the first substantially straight configuration to the second substantially closed configuration as shown in FIG. 11B, housing 1170 may be moved over or about clip 1100. For example, housing 1170 may be pushed/pulled distally over closed legs 1120 and 1130 of clip 1100. An interior surface of housing 1170 may be sized so as to snuggly receive clip 1100 and surrounding folded airway 28. As such, housing 1170 may prevent undesired opening of clip 1100. After moving legs 1120 and 1130 from the first, substantially straight configuration to the second, substantially closed configuration shown in FIG. 11B, thereby folding and occluding airway 28, and after the optional placement of housing 1170 over clip 1100, a user may apply a proximally (or rotatably) directed force in the direction of arrow A on clip delivery device 1110. After sufficient force has been applied, clip 1100 may break off of clip delivery device 1110 at frangible distal portion 1180. As such, clip 1100 may be configured to remain within airway 28 to maintain occlusion. It is to be understood that clip 1100, may include agents or drugs to promote proper tissue healing or sealing such as, for example, antimicrobial agents, analgesics, biocompatible adhesives, and anesthetics, etc.

Figure 12:
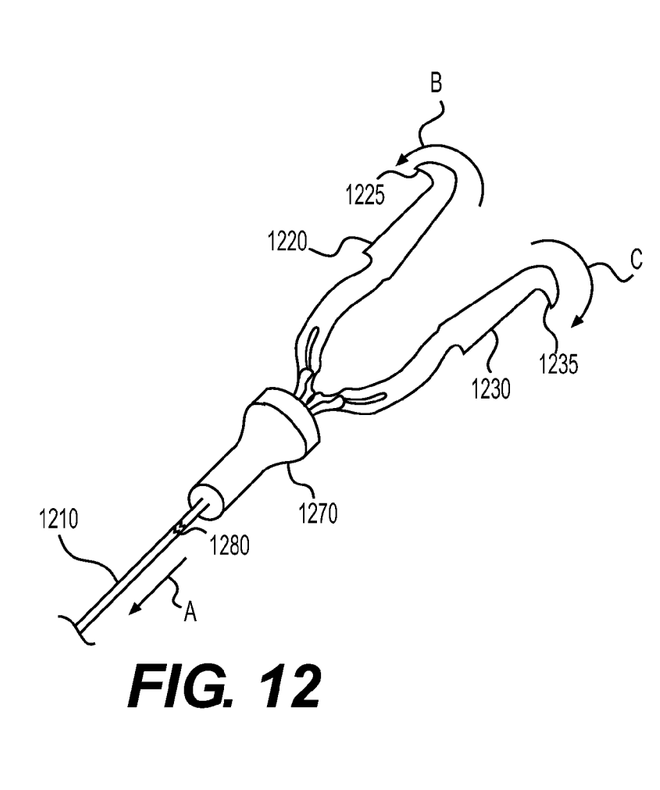
FIG. 12 is a diagrammatic view of an alternative exemplary device.
Figure 13:
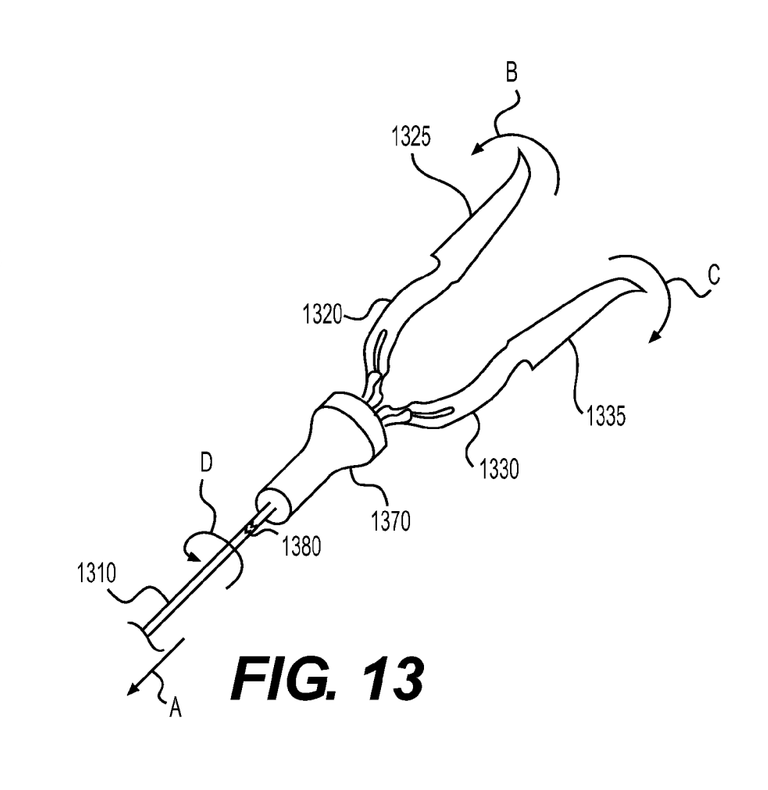
FIG. 13 is a diagrammatic view of an additional, alternative exemplary device.

FIGS. 12 and 13 depict alternative clip devices 1200 and 1300, respectively. Clips 1200 and 1300 may operate similarly to clip 1100, except for the manner in which airway 28 is occluded. For example, rather than folding legs of each respective clip 1200 and 1300 180°, each of the legs of clips 1200 and 1300 are provided with tissue engagement portions configured to collapse airway 28 into a sheath or housing. Clip 1200 may include first and second legs 1220 and 1230 (FIG. 12), whereas clip 1300 may include first and second legs 1320 and 1330 (FIG. 13). Each of clips 1200 and 1300 may be supported by a clip delivery device 1210 and 1310, similarly to clip delivery device 1110 described above. Clip delivery device 1210 may include frangible portion 1280, and clip delivery device 1310 may include frangible portion 1380.

In the embodiment shown in FIG. 12, however, each of legs 1220 and 1230 include hooks or sharpened tissue-grabbing distal ends 1225 and 1235. Ends 1225 and 1235 are configured to engage and embed in airway 28 when clip delivery device 1210 is pulled in the direction A shown. Additionally, each of legs 1220 and 1230 may be biased outward (e.g., self-expanding) as shown in FIG. 12. That is, upon deployment of clip 1200 into airway 28, legs 1220 and 1230 may spring apart in the directions of arrows B and C to engage and embed in tissue along airway 28. Once legs 1220 and 1230 have been embedded in airway 28, a user may pull clip delivery device 1210 in the direction A shown in FIG. 12. During this motion, airway 28, having ends 1225 and 1235 embedded therein is involuted (e.g., folded in on itself). As such, a distal portion of airway 28 is moved toward a proximal portion of airway 28 by moving a wall at the distal portion toward a central axis of the lumen and back towards the proximal portion. In this arrangement, a user may move (e.g., pull) clip delivery device 1210 until involuted airway 28 and legs 1220 and 1230 are received within sheath or housing 1270, thereby occluding airway 28. An interior surface of housing 1270 may be sized so as to snuggly receive clip 1200 and surrounding involuted airway 28. As such, housing 1270 may prevent undesired opening of clip 1200. After receipt of involuted airway 28 and clip 1200 in housing 1270, a user may apply a proximally directed force on clip delivery device 1210. After sufficient force has been applied, clip 1200 may break off of clip delivery device 1210 at frangible distal portion 1280. As such, clip 1200 may be configured to remain within airway 28 to maintain occlusion. It is to be understood that clip 1200, may include agents or drugs to promote proper tissue healing or sealing such as, for example, antimicrobial agents, analgesics, biocompatible adhesives, and anesthetics, etc.

In the embodiment shown in FIG. 13, each of legs 1320 and 1330 include elongate scoop-shaped tissue-grabbing sides 1325 and 1335. Sides 1325 and 1335 are configured to engage (e.g., snag, catch, and/or pierce) and draw in airway 28 when clip delivery device 1310 is rotated in direction D shown in FIG. 13. Said differently, as legs 1320 and 1330 are rotated, sides 1325 and 1335 are shaped so as to scoop and pull airway 28 into legs 1320 and 1330, via twisting force. It is understood that the directions of sides 1325 and 1335 may be reversed, and clip delivery device may be rotated in a direction opposite the direction of arrow D. Additionally, each of legs 1320 and 1330 may be biased outward (e.g., self-expanding) in the directions of arrows B and C as shown in FIG. 13. That is, upon deployment of clip 1300 into airway 28, legs 1320 and 1330 may spring apart to engage and embed in tissue along airway 28. Once legs 1320 and 1330 have been embedded in airway 28, a user may rotate or twist clip delivery device 1310 in direction D shown in FIG. 13. During this motion, airway 28, having side 1325 and 1335 embedded therein is twisted (e.g. folded) in on itself so as to collapse. In this arrangement, a user may move (e.g., pull) clip delivery device 1310 in direction A until folded airway 28 and legs 1320 and 1330 are received within sheath or housing 1370, thereby occluding airway 28. That is, after twisting airway 28, a user may pull the clip delivery device 1310 proximally so as move a distal portion of the airway 28 wall towards a proximal portion of the airway 28 wall. An interior surface of housing 1370 may be sized so as to snuggly receive clip 1300 and surrounding folded airway 28. As such, housing 1370 may prevent undesired opening of clip 1300. After receipt of twisted (e.g. folded) airway 28 and clip 1300 in housing 1370, a user may apply a proximally directed force on clip delivery device 1310. After sufficient force has been applied, clip 1300 may break off of clip delivery device 1310 at frangible distal portion 1380. As such, clip 1300 may be configured to remain within airway 28 to maintain occlusion. Additionally or alternatively, balloon 32, or any alternative expanding member, may include agents or drugs such as, for example, antimicrobial agents, analgesics, and anesthetics, etc. Further, it is to be understood that clip 1300, may include agents or drugs to promote proper tissue healing or sealing such as, for example, antimicrobial agents, analgesics, biocompatible adhesives, and anesthetics, etc.

While principles of the present disclosure are described herein with reference to illustrative embodiments for particular applications, it should be understood that the disclosure is not limited thereto. Rather, the devices and methods described herein may be employed to occlude any luminal tissue structure. Also, those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description. For example, while certain features have been described in connection with various embodiments, it is to be understood that any feature described in conjunction with any embodiment disclosed herein may be used with any other embodiment disclosed herein.

We claim:

1. A system, comprising:
a member extending along a longitudinal axis and
a manipulating portion coupled to a distal end of the member including a first actuatable member and a second actuatable member, each of the first actuatable member and the second actuatable member being configured to transition from a deployed configuration to a locking configuration, wherein in the deployed configuration, the first actuatable member and the second actuatable member each extends radially outwardly from the longitudinal axis;
wherein the first actuatable member includes a protrusion, the second actuatable member includes a cavity configured to receive the protrusion, and in the locking configuration, the protrusion is received by the cavity to form a one-way lock configured to prevent separation of the first actuatable member from the second actuatable member; and
wherein each of the first and second actuatable members is configured to rotate approximately 180° relative to the longitudinal axis and toward the distal end of the member so as to occlude the lumen.

2. The system of claim 1, wherein at least one of the first actuatable member and the second actuatable member includes a sharpened distal end configured to engage the wall.

3. The system of claim 1, wherein at least one of the first actuatable member and the second actuatable member is configured to transition from an undeployed configuration to the deployed configuration automatically.

4. The system of claim 1, wherein at least one of the first actuatable member and the second actuatable member is configured to transition from an undeployed configuration to the deployed configuration upon manual activation.

5. The system of claim 1, wherein the member includes a frangible portion adjacent the manipulating portion.

6. The system of claim 1, further including an introducer sheath including a retention member configured to anchor the introducer sheath in a natural body lumen having a wall, wherein the member extends through a working channel of the introducer sheath.

7. A method of manipulating a body lumen, comprising:
delivering a member into the body lumen, the member extending along a longitudinal axis, a distal end of the member coupled to a manipulating head having a first actuatable member and a second actuatable member, wherein the first actuatable member includes a protrusion, and the second actuatable member includes a cavity configured to receive the protrusion;
actuating the manipulating head to transition each of the first actuatable member and the second actuatable member from an undeployed configuration to a deployed configuration, wherein in the undeployed configuration the first actuatable member and the second actuatable member each extends substantially parallel to the longitudinal axis, and wherein in the deployed configuration, the first actuatable member and the second actuatable member each extends radially outwardly from the longitudinal axis;
in the deployed configuration, engaging tissue defining the lumen with each of the first actuatable member and the second actuatable member; and
after engaging tissue with each of the first actuatable member and the second actuatable member, transitioning the first actuatable member and the second actuatable member into a locking configuration to occlude the lumen, wherein the protrusion of the first actuatable member is received by the cavity of the second actuatable member in the locking configuration to form a one-way lock that prevents separation of the first actuatable member and the second actuatable member, and transitioning the first actuatable member and the second actuatable member into the locking configuration to occlude the lumen includes rotating a distal end of each of the first actuatable member and the second actuatable member approximately 180° relative to the longitudinal axis and toward the distal end of the member.

8. The method of claim 7, wherein the first actuatable member and the second actuatable member are automatically or manually actuated.

9. The method of claim 7, wherein the first actuatable member is rotated in a first direction, and the second actuatable member is rotated in a second direction that is opposite of the first direction.

10. The method of claim 9, further including sliding a housing over the first actuatable member and the second actuatable member when the first actuatable member and the second actuatable member are in the locking configuration.

11. The method of claim 10, wherein in the locking configuration, each of the first actuatable member and the second actuatable member extends substantially parallel to the longitudinal axis.

12. The method of claim 11, further including:
applying a proximally-directed or a rotationally-directed force to the member, to sever a frangible link disposed proximally of the manipulating head, to leave the manipulating head in the body lumen; and
removing the member from the body lumen.

13. The method of claim 12, wherein at least a portion of the manipulating head includes a biocompatible adhesive.

14. The method of claim 13, wherein the body lumen is a lung airway.

15. A system, comprising:
a member extending along a longitudinal axis; and
a removable clip coupled to a distal end of the member via a frangible link, the removable clip including a first arm and a second arm, each configured to transition from a deployed configuration to a locking configuration, wherein in the deployed configuration the first arm and the second arm each extends radially outwardly from the longitudinal axis;
wherein the first arm includes a protrusion, the second arm includes a cavity configured to receive the protrusion, and in the locking configuration, the protrusion is received by the cavity to form a one-way lock configured to prevent separation of the first arm from the second arm; and
the system further including a housing configured to slide over the first arm and the second arm when the first arm and the second arm are in the locking configuration to maintain the first arm and the second arm in the locking configuration.

16. The system of claim 15, wherein a distal end of the first arm is configured to rotate from the deployed configuration in a first direction toward the distal end of the member, and a distal end of the second arm is configured to rotate from the deployed configuration in a second direction, opposite of the first direction, toward the distal end of the member, wherein rotation of the distal ends of the first arm and the second arm cause the protrusion to be received by the cavity.

17. The system of claim 15, wherein the first arm and the second arm form a Y-shape in the deployed configuration, and wherein the first arm and the second arm are substantially parallel to one another in the locking configuration.

18. The system of claim 15, wherein at least a portion of the removable clip includes a biocompatible adhesive.

* * * * *